: US005429122A

United States Patent [19]
Zanen et al.

[11] Patent Number: 5,429,122
[45] Date of Patent: Jul. 4, 1995

[54] INHALER DEVICES PROVIDED WITH A RESERVOIR FOR SEVERAL DOSES OF MEDIUM FOR INHALING, TRANSPORTING DEVICE, WHIRL CHAMBER

[76] Inventors: Pieter, Zanen, Sikkelveld 27, NL-3993 RH Houten; Adrianus Plomp, Hulstweg 70, NL-1871 TJ Schoorl; Gerhardus A. Boon, Haremakers 52, NL-1531 LC Wormer; Roy van Swieten, Kerkstraat 18, NL-5253 AP Nieuwkuyk, all of Netherlands

[21] Appl. No.: 42,245

[22] Filed: Apr. 2, 1993

Related U.S. Application Data

[63] Continuation-in-part of Ser. No. 859,433, May 26, 1992.

[30] Foreign Application Priority Data

Sep. 26, 1990 [NL] Netherlands ............... 9002103
Jul. 15, 1991 [NL] Netherlands ............... 9101245
Sep. 20, 1991 [NL] Netherlands ............... 9101593

[51] Int. Cl.[6] .......... A61M 15/00; A61M 16/00; B05D 7/14; B05D 83/06
[52] U.S. Cl. .............. 128/203.15; 128/200.22
[58] Field of Search ............. 128/203.15, 203.21, 128/203.12, 203.23, 200.14, 200.21, 200.22; 604/58

[56] References Cited

U.S. PATENT DOCUMENTS

| 1,459,478 | 6/1923 | Page . | |
| 2,581,182 | 1/1952 | Fields | 128/206 |
| 4,274,403 | 6/1981 | Struve | 128/203 |
| 5,176,132 | 1/1993 | Drought et al. | 128/203.21 |

FOREIGN PATENT DOCUMENTS

| 211595 | 2/1987 | European Pat. Off. . |
| 2347939 | 11/1977 | France . |
| 1118341 | 4/1965 | United Kingdom . |
| 1515265 | 6/1978 | United Kingdom . |
| 2165159 | 4/1986 | United Kingdom . |

OTHER PUBLICATIONS

English Language Version of the International Search Report PCT/EP91/01884.

*Primary Examiner*—Kimberly L. Asher
*Attorney, Agent, or Firm*—Webb Ziesenheim Bruening Logsdon Orkin & Hanson

[57] ABSTRACT

The present invention provides an inhaler device for inhaling an aerosol in a desired dosage, comprising a housing in which is received a reservoir of powder or liquid, an inhaling piece placed on the housing and a mechanism for transporting the powder or liquid from the reservoir to the inhaling piece in a dosage required for the aerosol.

14 Claims, 8 Drawing Sheets

INHALER DEVICES PROVIDED WITH A RESERVOIR FOR SEVERAL DOSES OF MEDIUM FOR INHALING, TRANSPORTING DEVICE, WHIRL CHAMBER

RELATED APPLICATION

This is a continuation-in-part of U.S. application Ser. No. 07/859,433, filed May 26, 1992 which is a continuation of International Application No. PCT/EP91/01884 filed Sep. 26, 1991, now abandoned.

BACKGROUND OF THE INVENTION

1. Field of the Invention

The present invention relates to inhaler devices, in particular inhaler devices with which several doses can be administered. With such inhaler devices an aerosol is administered as medicine to the lungs, particularly the alveolar zone, by inhalation through nose or mouth.

2. Prior Art

Existing systems typically provide a single dose of an aerosol, whereafter a capsule is thrown away, which is harmful to the environment. Inhaler devices, for instance for CNSLD patients, wherein at each inhalation a capsule is placed therein, are frequently used in practice.

Inhaler devices for several doses are still only commercially available on a limited scale. There are problems with these known inhaler devices in respect of their manageability and size, the required suction force on a mouth or nose piece and/or the accuracy of dosing.

Known inhaler devices for several doses are awkward to use and/or consist of a relatively large number of components, whereby manufacture becomes time-consuming and expensive. Such an inhaler device is known from EP-A-211595.

SUMMARY OF THE INVENTION

A first embodiment of the present invention provides an inhaler device for inhaling an aerosol in a desired dosage, comprising a housing in which is received a reservoir of powder or liquid, an inhaling piece placed on the housing and a mechanism for transporting the powder or liquid from the reservoir to the inhaling piece in a dosage required for the aerosol.

A second embodiment of the present invention has for its object to obviate one or more of the above stated problems and provides a device for inhaling an aerosol, comprising:

- a reservoir for storing a supply of medium for inhaling;
- an inhaling piece for sucking air along with a dose of medium for inhaling; and
- transporting device for transporting a dose of medium for inhaling out of the reservoir, wherein a whirl chamber is incorporated in the inhaling piece for taking up the medium into the indrawn air with only a small suction force.

The present invention provides an inhaler device that can be used in different positions. The operation of the inhaling piece, the transporting means and/or the whirl chamber are not adversely affected by the position of the inhaler device relative to the direction of the force of gravity.

The whirling and high speed of the air are advantageous in obtaining particles for inhaling of a sufficiently small diameter (for instance smaller than 7, 5, or 1 $\mu$m).

The medium in the reservoir usually also comprises carrier material to cause the medium to flow easily, particularly from the reservoir to the whirl chamber where the particles for inhaling are then separated from the carrier particles (of usually greater diameter) by the shear forces generated by the air. Also when the medium for inhaling does not include any carrier material, shear forces have to be applied thereto, since such inhaling medium is composed of complexes of relatively large diameter, for instance greater than 7 $\mu$m. For inhalation into the alveolar zone the particle diameter also have to be reduced. With both types of medium there normally, remains a non-inhalable fraction of, for example, 20% by vol.

Transporting of the medium for inhaling preferably takes place by means of a screw or worm since, as has been found in tests, an accurate dose of medium can be transported herewith. One embodiment of the present invention uses a screw or worm as a transporting means, wherein a thickness of a threshold between the reservoir and the whirl chamber is less than the pitch of the thread on the worm.

Further preferred embodiments relate to the desired whirling of the air and the compactness of the inhaler device.

In preference the inhaler device comprises two or more mutually interchangeable reservoirs with different medium. A patient then only needs to carry one inhaler device on his/her person, even when (s)he has to inhale different types of medium. Such reservoirs can be provided in simple manner with a bayonet fitting for coupling to the remaining part of the inhaler device according to the present invention.

Inhaler devices provided with a mixing chamber, wherein at each inhalation a capsule with a dose of medium is introduced, in addition to a reservoir for several doses of medium for inhaling are widely available, for instance for CNSLD patients. The medium for inhaling typically comprises a powder which during inhalation must be present in the air in a particular diameter of, for instance, less than 10 $\mu$m, or less than 7, 5, or 1 $\mu$m. To improve the transporting properties of the powder, carrier material can be incorporated therein with a particle diameter greater than the above mentioned diameter. Also when no carrier material is included in the powder, complexes of particles occur easily in the aerosol which have a diameter greater than above stated. Particles with a greater diameter than the above stated are undesirable in the aerosol as they cannot exert any medicinal effect but can still result in irritations of the bronchial tubes, oral cavity and/or pharynx.

A third embodiment of the present invention provides an inhaler device for inhaling an aerosol, comprising:

- a suction piece for sucking in the aerosol;
- a mixing chamber for mixing sucked in air and medium for taking up air; and
- separating device for separating that fraction of the aerosol whereof the particles have a diameter greater than a predetermined value.

It will be apparent that the present invention is not limited to the case wherein the medium is in powder form. Use of the device according to the present invention is equally conceivable for vaporized (liquid) medium.

BRIEF DESCRIPTION OF THE DRAWINGS

Further advantages, features and details of the present invention will be elucidated in the light of a description of the preferred embodiments thereof with reference to the annexed drawings, in which.

DESCRIPTION OF THE PREFERRED EMBODIMENTS

Figure 1:
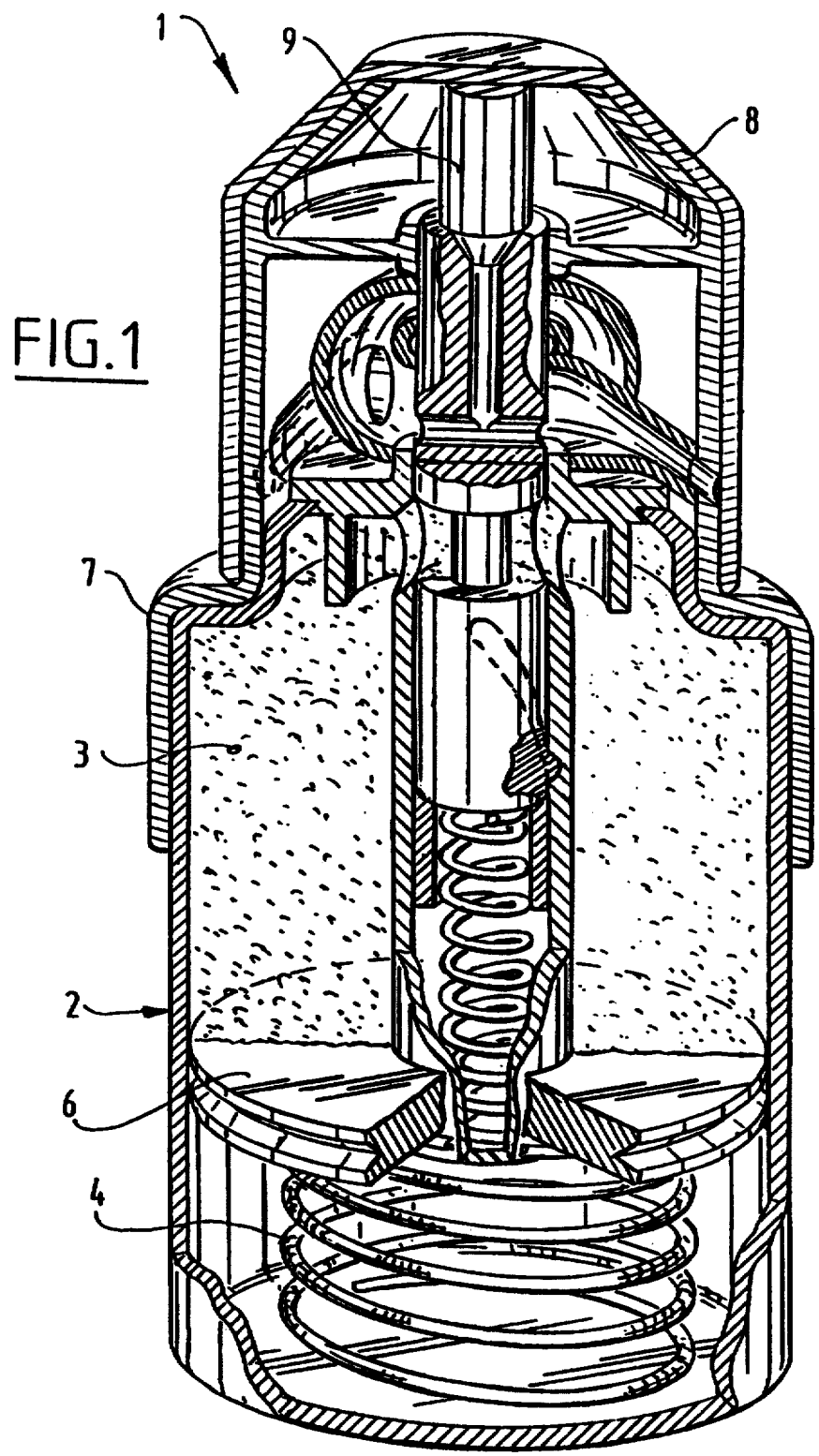
FIG. 1 shows a view, partly in section and partly in perspective, of a preferred embodiment according to the present invention in closed situation.

An inhaler device 1 (FIGS. 1–3) according to the present invention comprises a housing 2 in which a reservoir 3 of inhalable material, which is medicinal in the embodiment shown, is held in a compressed stated. Placed on the housing 2 is an inhaling piece 7, for example joined thereto in a manner not shown with a snap-on connection, so that after the reservoir has been emptied the inhaling piece can be placed on a new reservoir. The inhaling piece 7 is intended for placing on nose or mouth in order to be then sucked on. Placed over the inhaling piece 7 is a removable closing cap 8 provided with a protruding pin 9.

Figure 2:
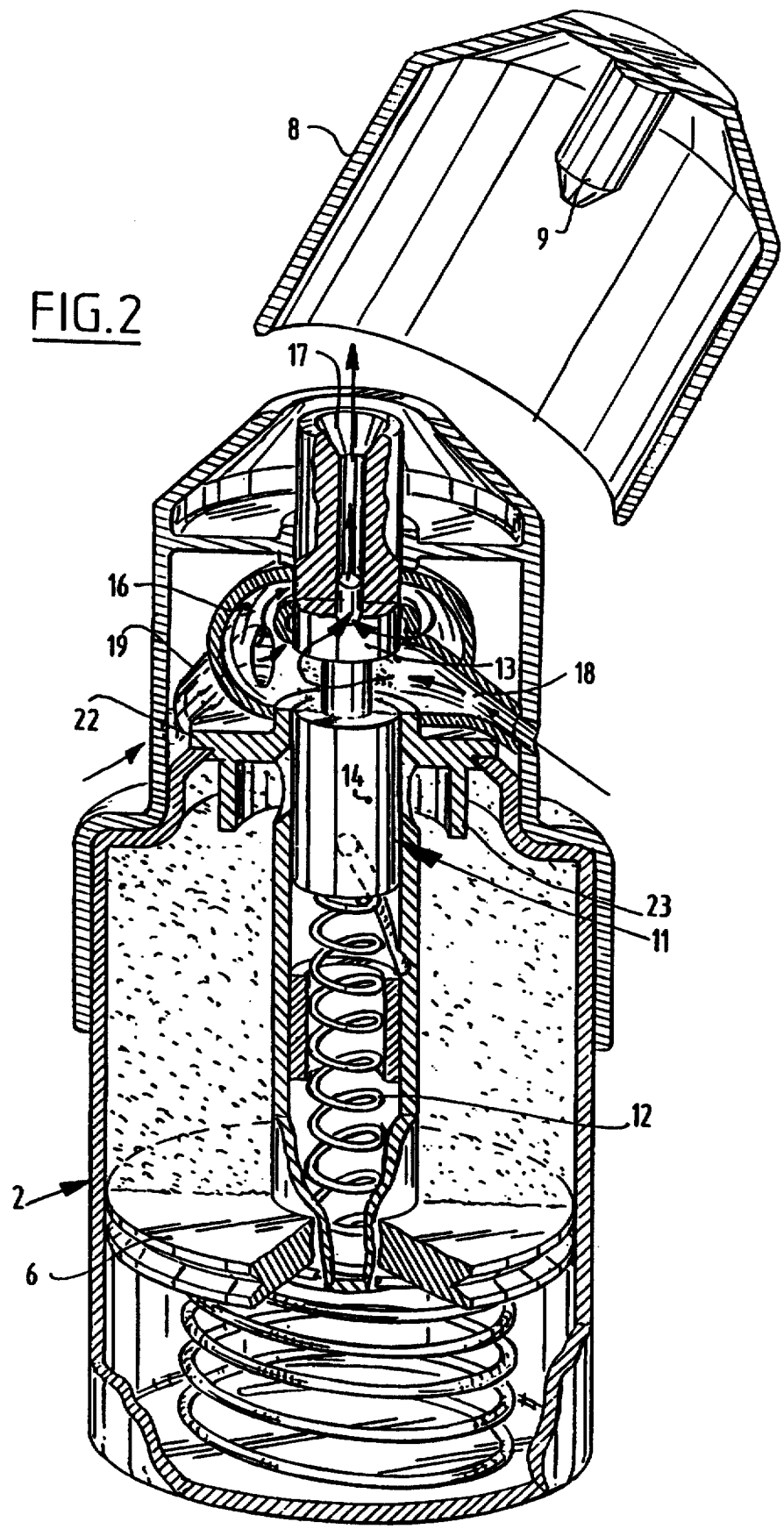
FIG. 2 is a view of FIG. 1 in the ready-for-use situation.

As will be apparent particularly from FIG. 2, when the closing cap 8 is removed, a plunger 11 is moved upward by means of the spring force of a second coil spring 12. The plunger 11 is provided with a recess between a top piece 13 and a bottom piece 14, wherewith a dose of powder can be transported in the desired dosage from the reservoir to a mixing space 16. As is indicated with the arrows, when the opening 17 is sucked on, suction takes place through three channels, of which the channels 18 and 19 are visible in the figure, and via whirling of the air a good mixing of the powder and the air is obtained in the desired manner.

In preference the pin portion 9 of the closing cap 8 is provided with a tapering portion which fits into the conical opening 17 so that when the closing cap 8 is arranged the up and downward movable plunger 11 provided with a central channel 21 and the recess can be moved into the rest position show in FIG. 1.

For guiding the powder to the recess in the plunger 65 the housing 2 is preferably provided with an upper piece 22 provided with collar-like portion 23 which protrudes into the powder reservoir.

So that the powder-form material is carried well by the plunger, the latter is provided with a protrusion guided in a groove 24 that is arranged in the cylinder-shaped guiding 25 for the plunger, wherein this groove 24 causes the plunger to rotate slightly.

Figure 3:
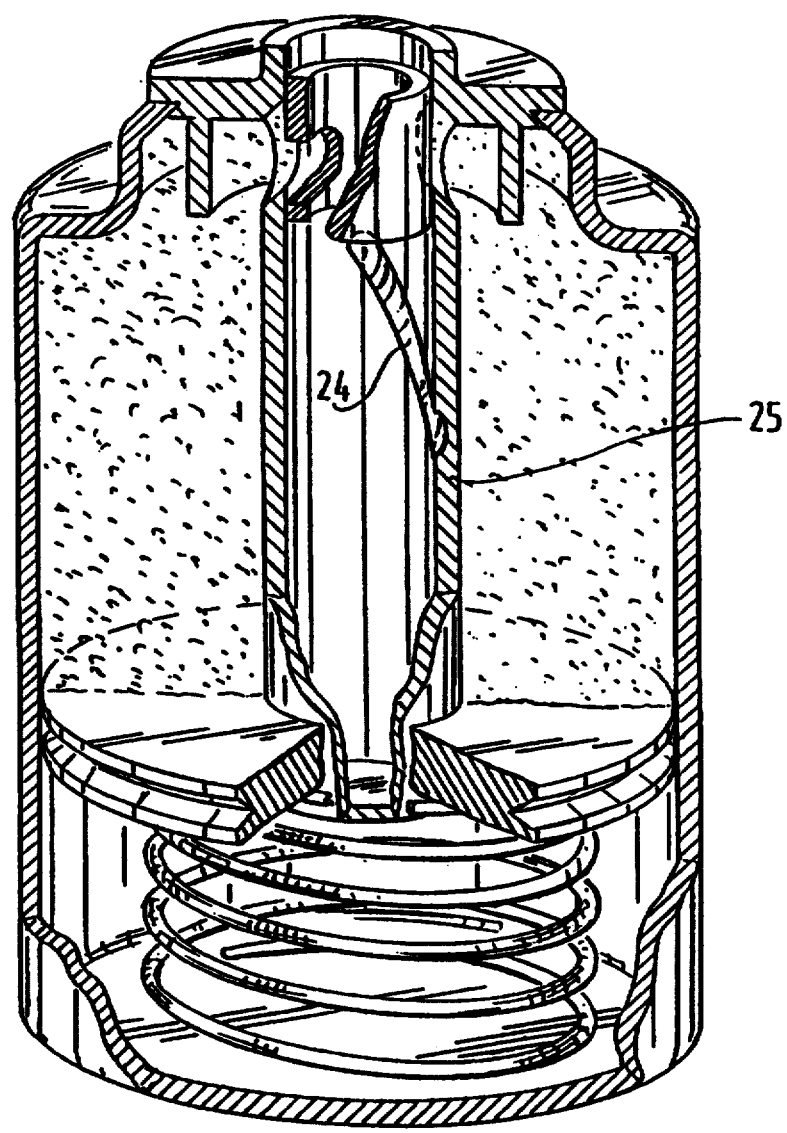
FIG. 3 shows a view, partly in section and partly in perspective, of the embodiment of FIG. 1 and FIG. 2 for elucidation of several details thereof.
Figure 4:
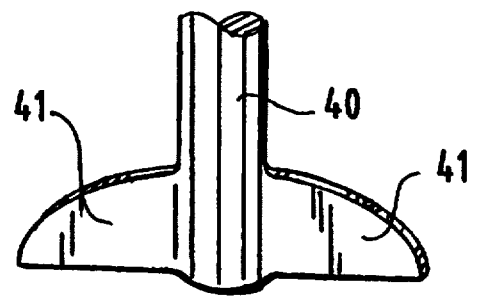
FIG. 4 shows a view of an element to be included in the embodiment of FIGS. 1–3.

In a further embodiment of the present invention (not shown), a shaft 40 provided with wing-like elements 41 can be included at the center line of the device shown in FIGS. 1–3. Preferably a rotating mechanism is provided such that for every dose shaft 40 is rotated and powder is stirred by elements 41 whereby the flow of the powder is improved. The rotating mechanism can correspond to such mechanism as used in a ballpoint pen for rotating the writing element thereof.

The present inhaler device is suitable for giving a large number of doses and therefore for prolonged use. It can be manufactured from a comparatively small number of components, preferably of plastic.

Figure 5:
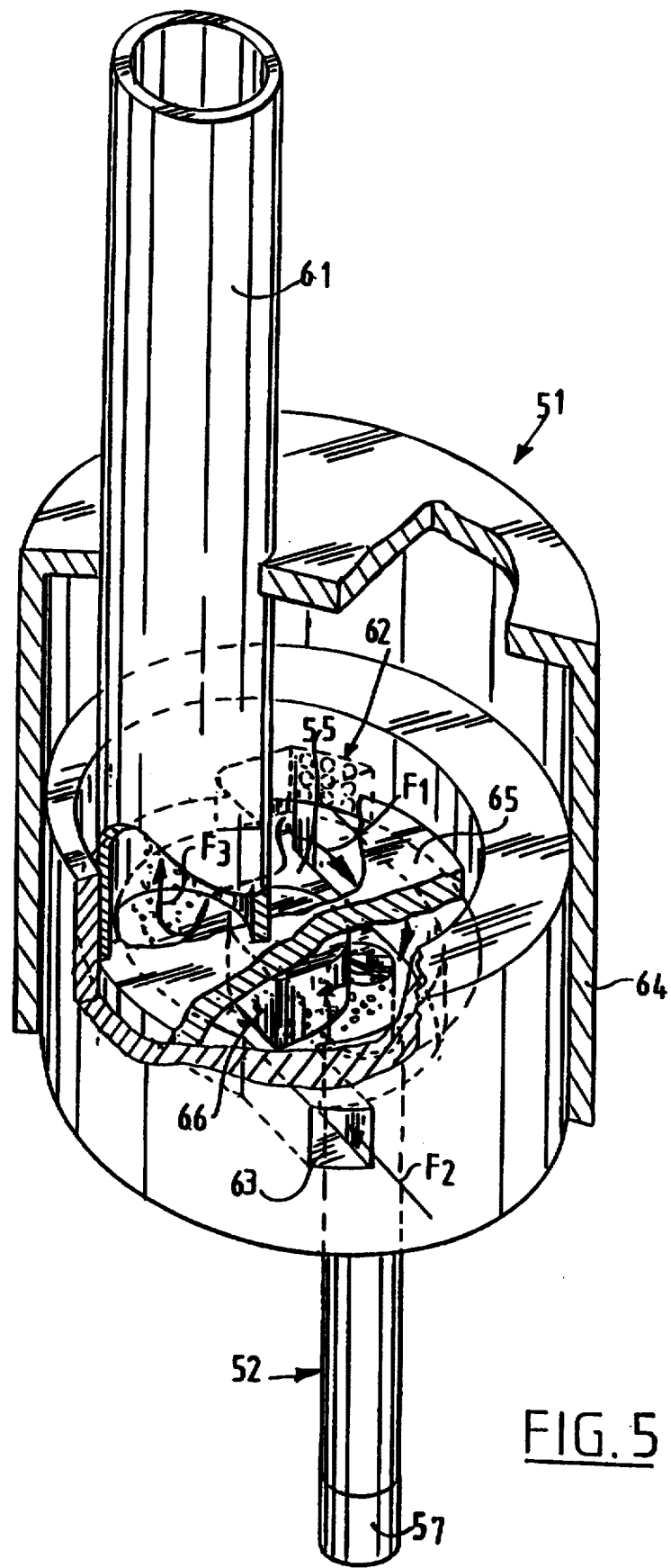
FIG. 5 shows a partly broken away view in perspective of a second preferred embodiment of the inhaler device according to the present invention.
Figure 6:
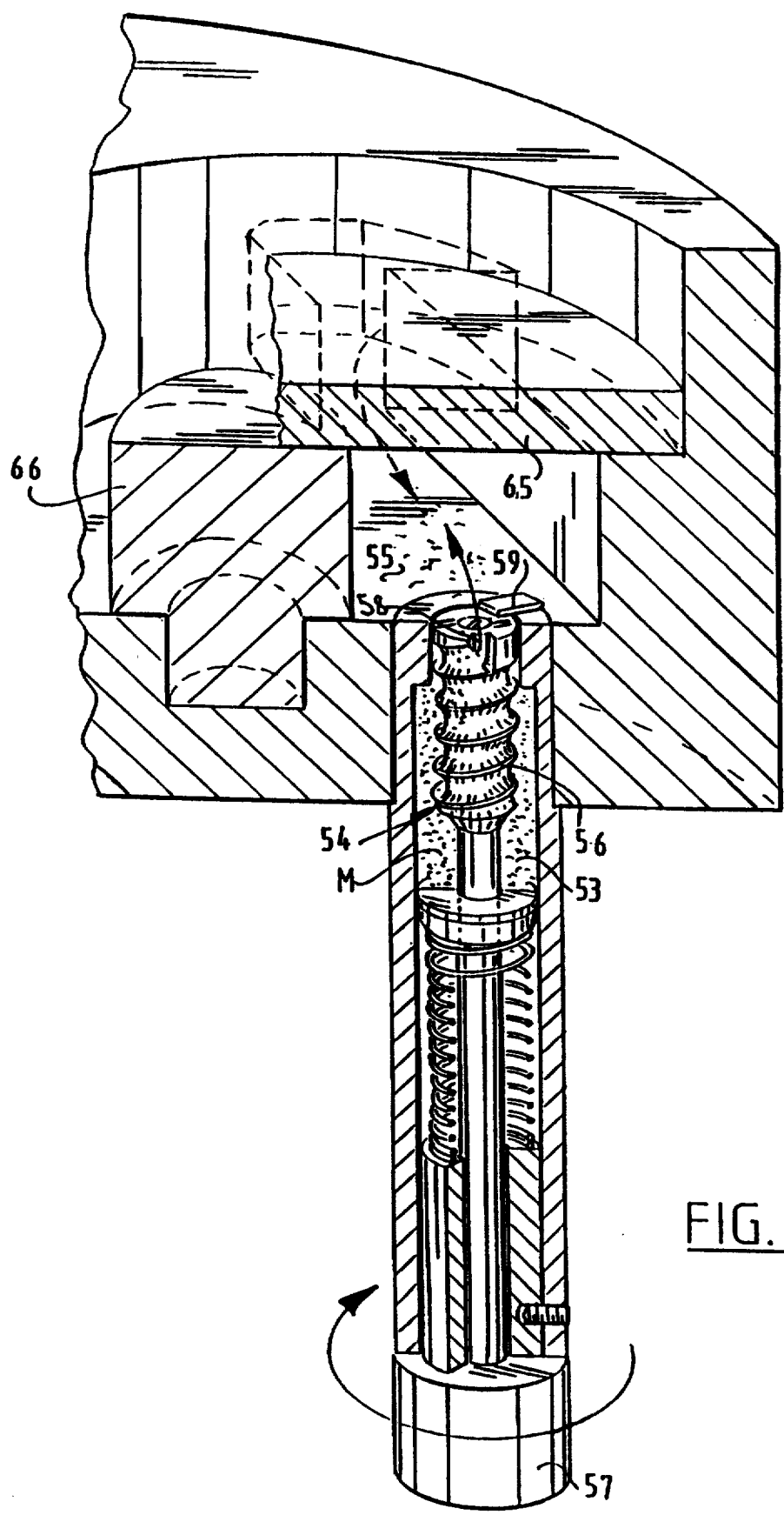
FIG. 6 is a view, partly in perspective and partly in section, of detail II of FIG. 5.

A second embodiment, an inhaler device 51 (FIG. 5), is provided with a part 52 (FIG. 5, FIG. 6) in which is received a reservoir 53 for medium for inhaling in addition to a transporting mechanism 54 for transporting the medium out of the reservoir to a whirl chamber 55. The material for inhaling comprises carrier particles which are of minor importance in the effect on the bronchial tubes of a patient. These carrier particles are necessary however in order to prevent the medium M for inhaling from coagulating and thereby becoming barely transportable.

For transporting the medium M in doses of precise size a screw or worm 56 is preferably used which can be operated using a rotating knob 57. Worm or screw 56 has threads inherent in all worms or screws, and as the threads are in contact with the medium M, the medium M is transported along the threads of screw or worm 56 as knob 57 is turned. The medium M is thus transported out of the reservoir 53 into the whirl chamber 55 through opening 58. It has been found in tests that such a transporting mechanism is capable of transporting a medium M with an accuracy of less than 5% out of the reservoir 53 into the whirl chamber 55 at each revolution of the opening 58 away from and up to a closing member 59 for this opening.

The inhaler device is provided with an inhaling piece 61 for sucking in air via the nose or mouth of a patient along two feed channels 62 and 63 which are arranged in a peripheral wall 64 of the inhaler device. A flow of air, as designated with arrows $F_1$, carries the medium brought into the whirl chamber 55 under cover plate 65 along a guide means 66 and then collides with the air flow designated with arrow $F_2$ which is drawn in along feed channel 63. With a comparatively small suction force great air speeds occur here, in addition to whirls when these air flows $F_1$ and $F_2$ collide with one another. Shear forces hereby occur which separate the particles with medicinal effect from the carrier particles which usually have a greater diameter than that of the medicinal particles.

Figure 7B:
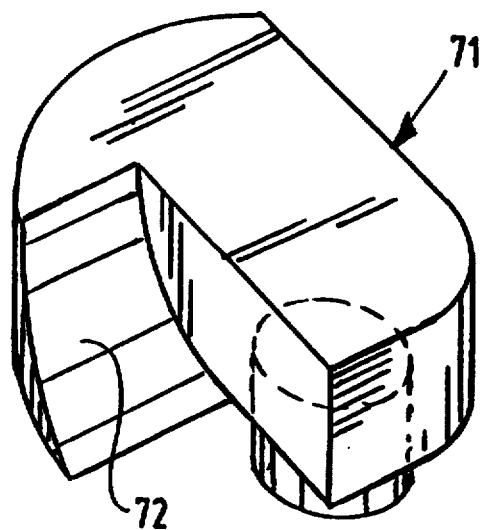
FIG. 7A and FIG. 7B respectively show elements which can be incorporated in the embodiment as shown in FIG. 5 and FIG. 6.
Figure 7A:
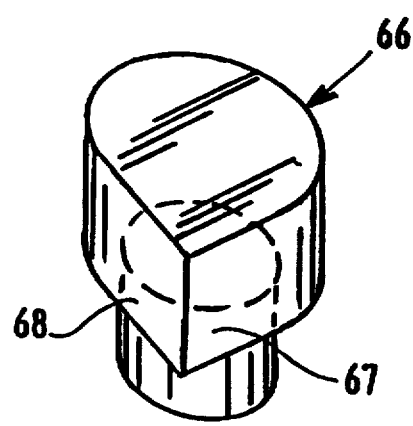

The member 66 for guiding the air (FIG. 7A) is provided on the side facing the feed channel 62 with a rounded form, while the side facing the feed channel 63 is sharp-edged and the angle is formed by flat wall portions 67 and 68 so that the air flow $F_2$ collides with the air flow $F_1$ transversely.

In a further embodiment (not shown), the inhaler devices according to the present invention is provided with a guide means 71 for guiding the air (FIG. 7B) partially similar to the guide means 66, but which is additionally provided with an air guide portion 72 rising in the direction of the inhaling piece 61 and preventing unwanted air, as indicated with arrow $F_3$ in FIG. 1, on the side of the guide means 71 remote from the doses of medium for inhaling from passing into the inhaling piece 61. An inhaler device provided with such a guide means 71 therefore requires an even smaller suction force, which is particularly important in the case of children and older patients with lung disorders.

The inhaler device according to the shown and described embodiment has, among others, the following advantages:

the inhaler device is compact of structure and has a size such that it can easily be held in the hand;

the inhaler device can be used in any desired position, with the inhaling piece horizontal or oriented upward or downward;

the inhaler device requires little suction force, while great shear forces are applied to the medium or powder so that the medicinal particles are released from the carrier particles.

Figure 8:
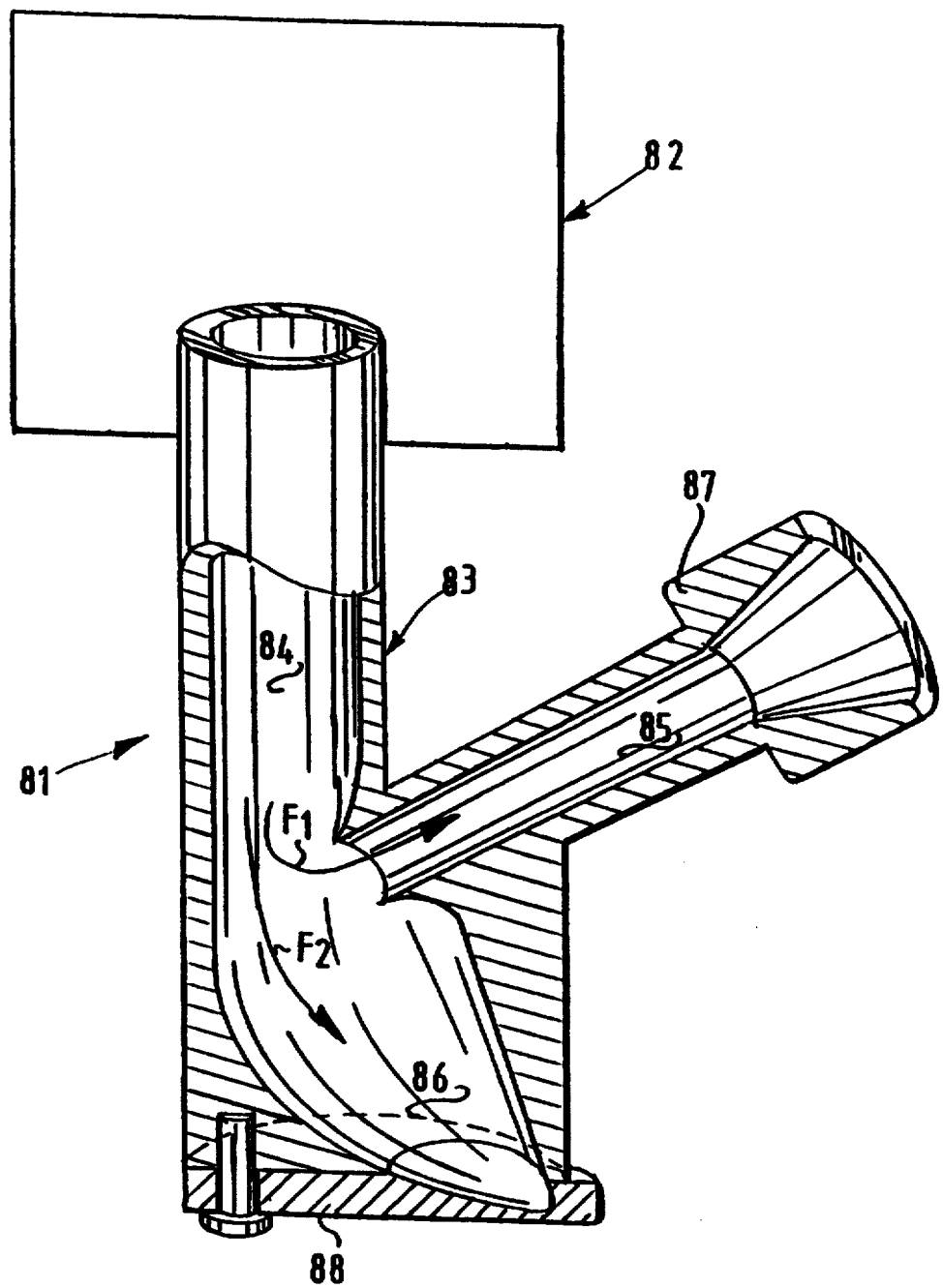
FIG. 8 shows a side view of a third embodiment, partly in section, of the inhaler device according to the present invention.

A third embodiment of an inhaler device 81 (FIG. 8) according to the present invention comprises a schematically designated mixing chamber 82 in which a dosage for inhaling is mixed with air drawn into the mixing chamber 82 in a manner not shown. The inhaler device 81 can further be provided with a reservoir in which is received a supply of medium for inhaling, in addition to transporting means, likewise not shown, for transporting one dose of medium at a time out of this reservoir into the mixing chamber.

Coupled to the mixing chamber 82 is a suction piece 83 comprising an inlet channel 84, an outlet channel 85 and a collecting chamber 86. The suction piece 87 is sucked on by the patient via nose or mouth. A fraction of the aerosol, designated with arrow $B_2$ whereof the particles have a comparatively large diameter, for example greater than 10, 7, 5 or 1 μm, does not however reach the outlet channel 85 of the mass of the particles. These particles from the fraction $B_2$ are collected at the bottom of the collecting chamber 86 which must be emptied from time to time by releasing the cover 88.

With the inhaler device (third embodiment) according to the present invention now proposed and still to be realized in practice, the angle enclosed by the center lines of the outlet channel 85 and the inlet channel 84 has a value of approximately 60° that is, the change of direction amounts to roughly 120°. The inlet channel is initially envisaged as having a diameter of approximately 1 cm, the outlet channel as having a diameter of 0.8 cm and the inlet channel as having a length of about 5 cm. The preferred embodiment shown is preferably realized in plastic.

Figure 9:
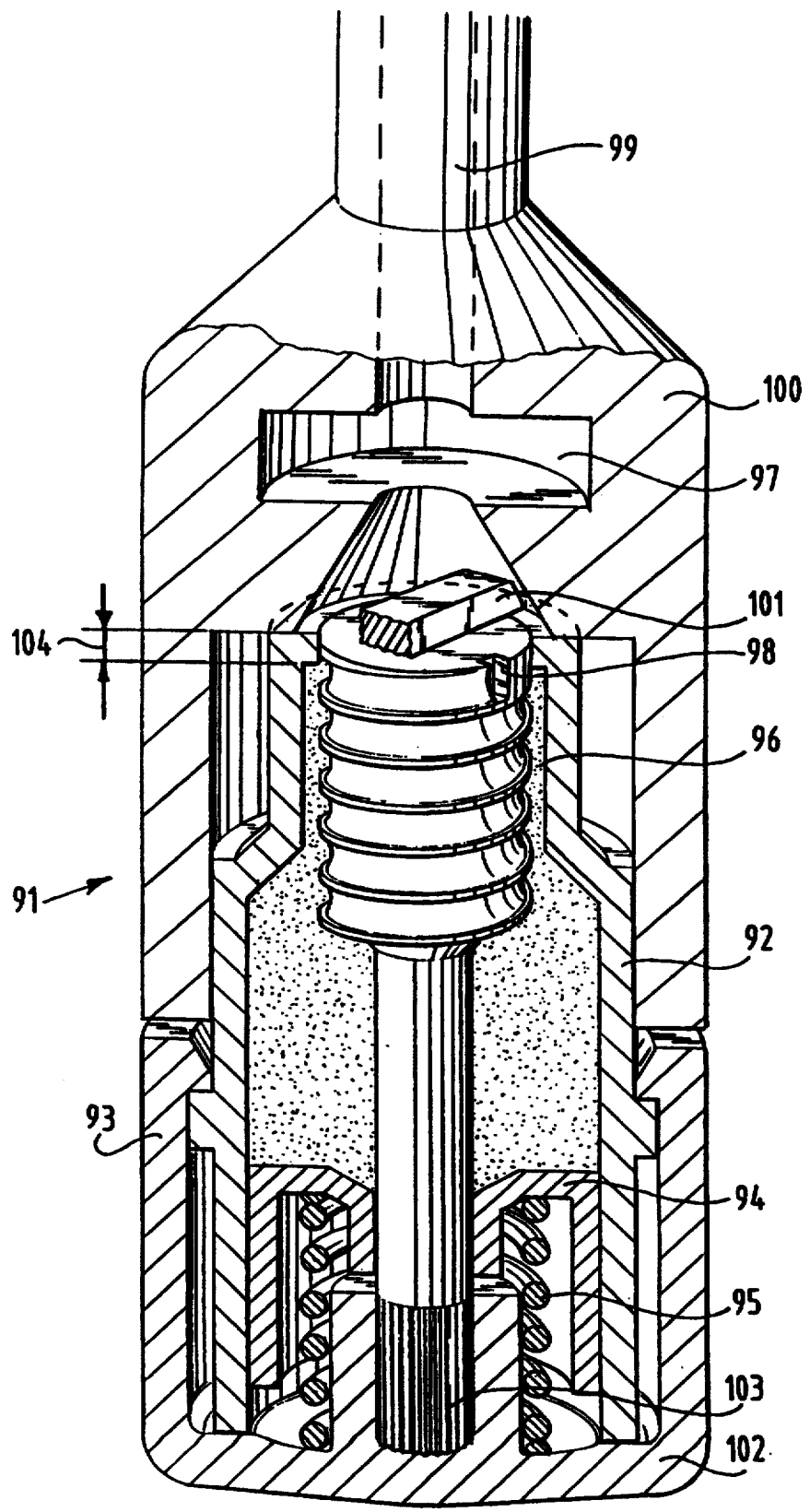
FIG. 9 shows a partially broken away view of a fourth preferred embodiment of the inhaler device according to the present invention.

A fourth embodiment of inhaler device 91 is shown in FIG. 9. The inhaler device 91 includes a housing 92 in which a reservoir 93 of inhalable material, which may be medicinal, is held in a compressed state. Compression within the reservoir 93 is maintained by a movable base 94 biased by spring 95. A transporting screw or worm 96 is provided within the reservoir 93 for transporting the medium out of the reservoir 93 into a whirl chamber 97 through an opening 98. The whirl chamber 97 is coupled to an inhaling conduit 99 which operates substantially the same as the opening 17 or inhaling piece 61 described above. The inhaling conduit 99 and the whirl chamber 97 are formed in an inhaling piece 100 which is placed on the housing 92. The connection between the inhaling piece 100 and the housing 92 may be a snap-on connection or the like so that after the reservoir 93 has been emptied, the inhaling piece 100 can be placed over a new reservoir 93.

A closing piece 101 is positioned to selectively seal off the opening 98 when the opening 98 is aligned with the closing piece 101. The screw or worm 96 is adapted to be rotated by a turning knob 102 connected to the screw or worm 96 through a spline connection 103.

In operation, knob 102 is turned to cause the transporting screw or worm 96 to rotate 180°. The screw or worm 96 is now positioned to an opposed sealed position wherein the closing piece 101 is aligned with the opening 98 to seal off the opening 98. This operation will effectively dispense one dosage of the medium of about 7 to 8 mg. into the whirl chamber 97.

In the inhaler device 91, the thickness, shown at 104, of the threshold of the housing 92 positioned between the reservoir 93 and the whirl chamber 97 is less than the pitch of the thread of the transporting screw or worm 96. Preferably, the thickness 104 of the threshold is less than 3 mm and preferably about 1 mm. This construction minimizes the difficulties in rotating the transporting screw or worm 96 due to the medium within the reservoir 93.

The present invention is not limited to the preferred embodiments shown and described. The rights are determined by the claims following hereinafter.

We claim:

1. A device for inhaling an aerosol comprising: p1 a) a housing which has therein a reservoir of an inhalable medium; p1 b) an inhaling piece placed on said housing; p1 c) a piston and a spring incorporated in said housing for holding the inhalable medium in said reservoir in a compressed state; and p1 d) means for transporting the inhalable medium from said reservoir to said inhaling piece in a dose required for the aerosol, said transporting means including a plunger provided with a recess and movable reciprocally counter to the pressure of a plunger spring between a first position wherein said recess is in communication with said reservoir and a second position wherein said recess is in communication with said inhaling piece; p1 e) wherein said plunger of said transporting means is reciprocally movable to said first position by means of a closing cap placed on said inhaling piece, wherein when said closing cap is removed said plunger is moved to said second position by said plunger spring and a dose of the inhalable medium is transported to said inhaling piece.

2. The inhaler device as claimed in claim 1 wherein the inhalable medium in said reservoir is a powder.

3. The inhaler device as claimed in claim 1 wherein said plunger includes protrusion means received in a groove for causing said plunger to rotate relative to said housing.

4. The inhaler device as claimed in claim 1 further including rotatable stirring elements extending into said reservoir.

5. A device for inhaling an aerosol, comprising: p1 a) a reservoir storing a supply of an inhalable medium; p1 b) an inhaling piece for sucking indrawn air, along with a dose of the inhalable medium, and having a whirl chamber incorporated therein; and p1 c) screw means for transporting a dose of the inhalable medium from said reservoir, said screw means including a rotatable worm positioned within said reservoir in contact with said inhalable medium, said worm including threads for conveying said inhalable medium, and a closing member between said worm and said inhaling piece, said worm including at least one opening at one end thereof which is movable between a position covered by said closing member and a position in communication with said whirl chamber wherein the inhalable medium is taken up in said inhaling piece along said threads of said worm with the indrawn air with only a small suction force.

6. The inhaler device as claimed in claim 5 further including a piston which is under spring pressure and holds the inhalable medium under pressure.

7. The inhaler device as claimed in claim 5 further including a whirl chamber having a first opening and a second opening, wherein air drawn in through said first opening moves a dose of the inhalable medium and subsequently collides with an air flow drawn in along said second opening, and wherein a whirling is excited such that the active constituents of the inhalable medium are released to a sufficient extent with sufficiently small diameter.

8. The inhaler device as claimed in claim 5 wherein a mouth of said inhaling piece is disposed eccentrically of a center line extending through said inhaler piece.

9. The inhaler device as claimed in claim 5 further including a guide means for guiding the air flow and arranged in the vicinity of the center of said inhaling piece.

10. The inhaler device as claimed in claim 9 wherein said guide means is provided with a rounded portion and with a sharp-edged portion.

11. The inhaler device as claimed in claim 9 wherein said guide means is provided with a guide portion for guiding said air flow upward to a mouth of said inhaling piece.

12. The inhaler device as claimed in claim 5 further including at least two mutually interchangeable reservoirs storing different inhalable media.

13. The inhaler device as claimed in claim 5 wherein the thickness of a partition between said whirl chamber and said reservoir is less than a pitch of said screw means.

14. A device for inhaling an aerosol, comprising: p1 a) a housing which has therein a reservoir of an inhalable medium; p1 b) an inhaling piece placed on said housing; p1 c) a piston and a spring incorporated into said housing for holding said inhalable medium in said reservoir in a compressed state; and p1 d) screw means in contact with said inhalable medium for transporting a dose of the inhalable medium from said reservoir to said inhaling piece, said screw means including threads for conveying said inhalable medium, said threads having a pitch, wherein the thickness of a threshold between said reservoir and said inhaling piece is less than said pitch of said threads of said screw means.

* * * * *

UNITED STATES PATENT AND TRADEMARK OFFICE
CERTIFICATE OF CORRECTION

PATENT NO. : 5,429,122

DATED : July 4, 1995

INVENTOR(S) : Pieter Zanen, Adrianus Plomp, Gerhardus A. Boon and Roy van Swieten It is certified that error appears in the above-indentified patent and that said Letters Patent is hereby corrected as shown below:

Title page, under section '[76] Inventors:', after "Pieter" delete ",".

Column 2 Line 13 after "normally" delete --,--.

Column 3 Line 38 "stated." should read --state.--.

Column 3 Line 57 after "air" insert --,--.

Column 3 Line 64 "show" should read --shown--.

Column 4 Line 10 after "dose" insert --,--.

Column 4 Line 66 "devices" should read --device--.

Claim 1 Line 29 Column 6 delete "p1" and begin a new paragraph with "a)".

Claim 1 Line 31 Column 6 delete "p1" and begin a new paragraph with "b)".

UNITED STATES PATENT AND TRADEMARK OFFICE
CERTIFICATE OF CORRECTION

PATENT NO. : 5,429,122

DATED : July 4, 1995

INVENTOR(S) : Pieter Zanen, Adrianus Plomp, Gerhardus A. Boon and Roy van Swieten It is certified that error appears in the above-indentified patent and that said Letters Patent is hereby corrected as shown below:

Claim 1 Line 32 Column 6 delete "p1" and begin a new paragraph with "c)".

Claim 1 Line 34 Column 6 delete "p1" and begin a new paragraph with "d)".

Claim 1 Line 42 Column 6 delete "p1" and begin a new paragraph with "e)".

Claim 5 Line 58 Column 6 delete "p1" and begin a new paragraph with "a)".

Claim 5 Lines 59-60 Column 6 delete "p1" and begin a new paragraph with "b)".

Claim 5 Line 62 Column 6 delete "p1" and begin a new paragraph with "c)".

Claim 14 Line 15 Column 8 delete "p1" and begin a new paragraph with "a)".

Claim 14 Line 17 Column 8 delete "p1" and begin a new paragraph with "b)".

UNITED STATES PATENT AND TRADEMARK OFFICE
CERTIFICATE OF CORRECTION

PATENT NO. : 5,429,122
DATED : July 4, 1995
INVENTOR(S) : Pieter Zanen, Adrianus Plomp, Gerhardus A. Boon and Roy van Swieten It is certified that error appears in the above-indentified patent and that said Letters Patent is hereby corrected as shown below:

Claim 14 Line 18 Column 8 delete "p1" and begin a new paragraph with "c)".

Claim 14 Line 20 Column 8 delete "p1" and begin a new paragraph with "d)".

Signed and Sealed this

Fifth Day of December, 1995

Attest:

BRUCE LEHMAN

Attesting Officer

Commissioner of Patents and Trademarks